(12) United States Patent
Jeanbourquin

(10) Patent No.: US 6,183,446 B1
(45) Date of Patent: *Feb. 6, 2001

(54) NEEDLE PROTECTION INJECTION DEVICES

(75) Inventor: Edgar Jeanbourquin, Neuendorf (CH)

(73) Assignee: Disetronic Licensing AG, Burgdorf (CH)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/208,078

(22) Filed: Dec. 9, 1998

(30) Foreign Application Priority Data

Dec. 11, 1997 (DE) .......................... 197 55 125.4

(51) Int. Cl.⁷ ...................................... A61M 5/32
(52) U.S. Cl. ...................... 604/198; 604/192; 604/263
(58) Field of Search ...................... 604/198, 192, 604/110, 197, 263; 128/919

(56) References Cited

U.S. PATENT DOCUMENTS

| | | |
|---|---|---|
| 4,592,745 | 6/1986 | Rex et al. . |
| 4,865,591 | 9/1989 | Sams . |
| 4,883,472 | 11/1989 | Michel . |
| 4,911,693 * | 3/1990 | Paris ........................ 604/192 |
| 4,946,446 * | 8/1990 | Vadher ...................... 604/198 |
| 4,973,318 | 11/1990 | Holm et al. . |
| 5,017,190 | 5/1991 | Simon et al. . |
| 5,084,060 | 1/1992 | Freund et al. . |
| 5,114,406 | 5/1992 | Gabriel et al. . |
| 5,273,544 | 12/1993 | van der Waal . |
| 5,279,579 * | 1/1994 | D'Amico ................. 604/192 |
| 5,279,585 | 1/1994 | Balkwill . |
| 5,292,314 * | 3/1994 | D'Alessio et al. ........... 604/198 |
| 5,295,976 | 3/1994 | Harris . |
| 5,320,609 | 6/1994 | Haber et al. . |
| 5,336,183 | 8/1994 | Greelis et al. . |
| 5,338,311 * | 8/1994 | Mahurkar ................. 604/195 |
| 5,370,629 | 12/1994 | Michel et al. . |
| 5,472,430 * | 12/1995 | Vaillancourt et al. ........ 604/198 |
| 5,496,293 | 3/1996 | Huggenberger . |
| 5,514,097 | 5/1996 | Knauer . |
| 5,549,558 * | 8/1996 | Martin ..................... 604/198 |
| 5,549,575 | 8/1996 | Giambattista et al. . |
| 5,573,510 * | 11/1996 | Isaacson ................... 604/198 |
| 5,582,598 | 12/1996 | Chanoch . |
| 5,591,136 | 1/1997 | Gabriel . |
| 5,591,138 * | 1/1997 | Vaillancourt .............. 604/198 |
| 5,593,390 | 1/1997 | Castellano et al. . |
| 5,643,214 | 7/1997 | Mashall et al. . |
| 5,658,259 | 8/1997 | Pearson et al. . |
| 5,674,204 | 10/1997 | Chanoch . |
| 5,679,111 | 10/1997 | Hjertman et al. . |
| 5,725,508 | 3/1998 | Chanoch et al. . |
| 5,728,074 | 3/1998 | Castellano et al. . |
| 5,743,889 | 4/1998 | Sams . |
| 5,807,346 | 9/1998 | Frezza . |
| 5,919,168 * | 7/1999 | Wheeler .................. 604/198 |
| 5,984,899 * | 11/1999 | D'Alessio et al. ........... 604/198 |

\* cited by examiner

*Primary Examiner*—John G. Weiss
*Assistant Examiner*—Cris L. Rodriguez
(74) *Attorney, Agent, or Firm*—Dorsey & Whitney LLP

(57) ABSTRACT

The present invention provides a needle protector for use with an injection device, wherein the needle protector includes a first sleeve, a second sleeve that can at least partially be slid into or over the first sleeve and a force element functioning between the two sleeves, wherein a pressure or trigger point has to be overcome to displace the second sleeve.

20 Claims, 3 Drawing Sheets

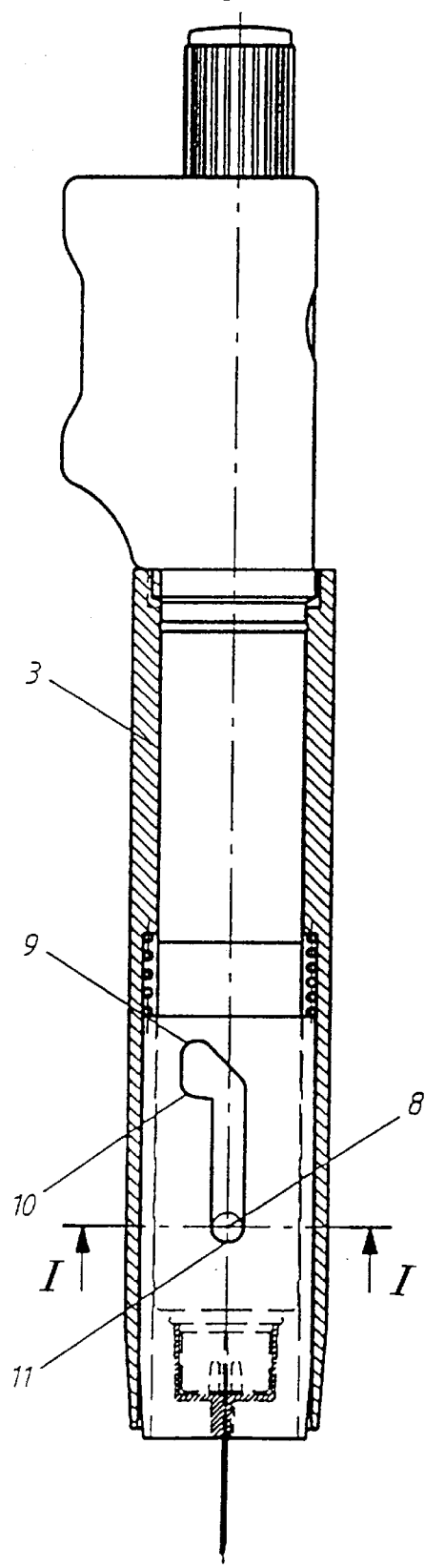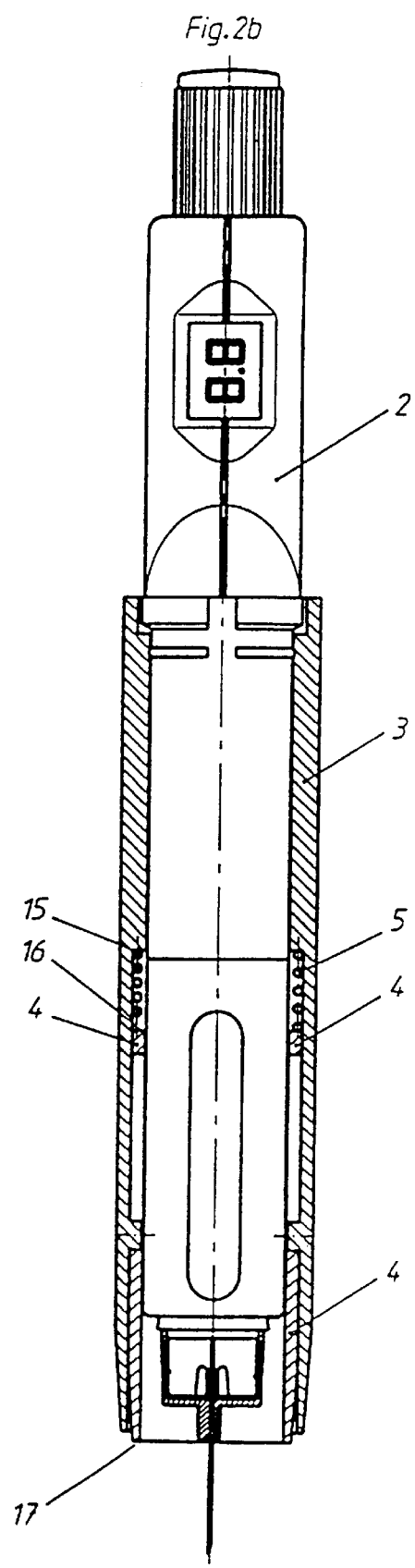

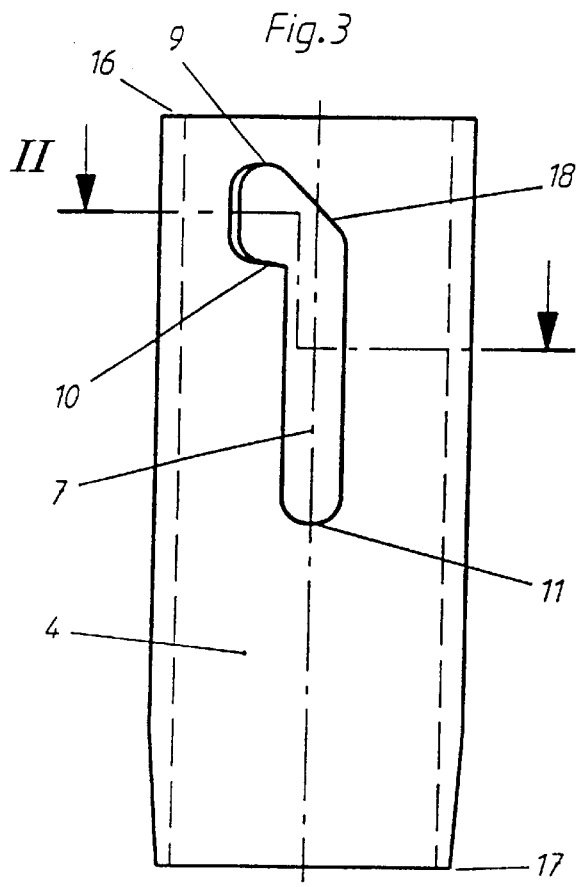
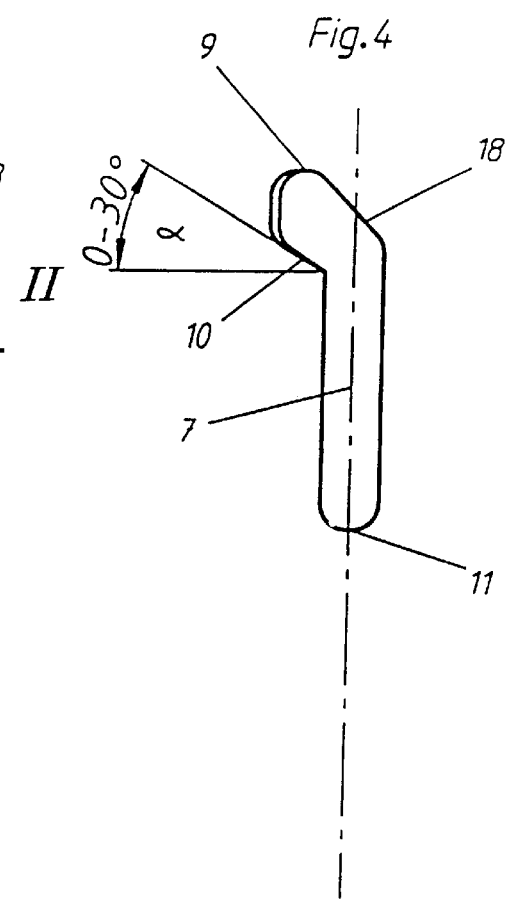
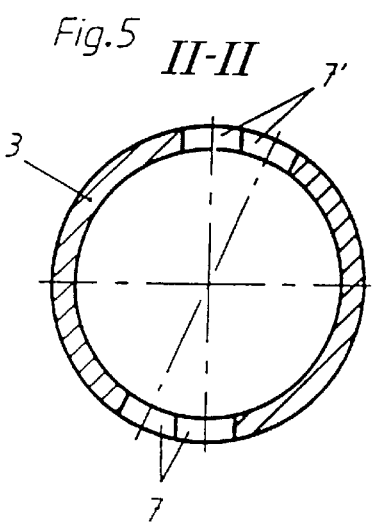
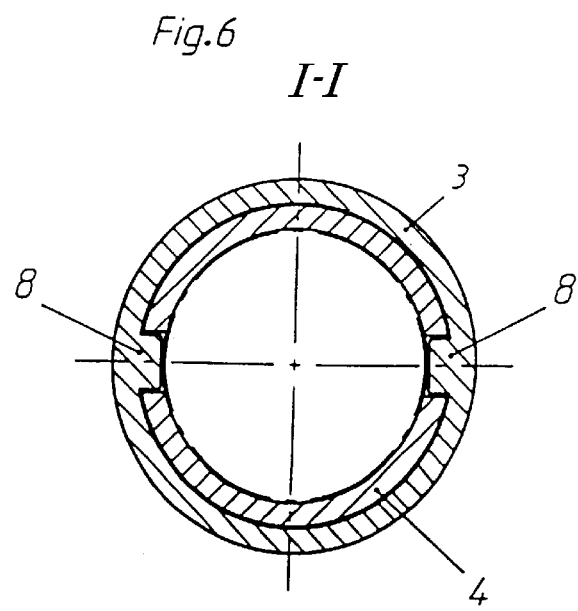

NEEDLE PROTECTION INJECTION DEVICES

PRIORITY CLAIM

This application claims the priority of German Application No. 197 55 125.4, filed Dec. 11, 1997, which is incorporated herein by reference.

BACKGROUND OF THE INVENTION

1. Field of the Invention

The present invention refers to a needle protection means for injection devices comprising a first sleeve, a second sleeve that can be slid into or over the first sleeve and a force element functioning between the two sleeves, wherein a pressure or trigger point must be overcome to displace the second sleeve Today, the term injection device is used for simple syringes as well as complex, dosable injection devices that, as their design resembles that of writing tools, are referred to as pens.

2. Description of Related Art

Such pens are known from WO 93/16740. They contain a sleeve-like main body which can be divided into two main areas: a distal area (facing away from the patient) containing a discharge mechanism and a proximal area (facing towards the patient) that contains the fluid to be administered. At the proximal end of the main body a needle and needle holder are attached that allow the discharge of the liquid from the device; such known needles are, for instance, PENFINE® needles as described in WO 95/01812.

In many cases, the liquids to be administered are not directly located in the main body but in an ampoule, with the liquid being stored between a piercable membrane and a displaceable piston.

By activating the discharge mechanism, the piston of the ampoule is pushed into the proximal direction so that fluid is discharged through the needle.

For psychological reasons, many patients find it difficult to inject themselves, as a fully visible needle has to penetrate the skin. Needle protection means that only enclose the needle and thus hide the needle from the patient's view during penetration are known from WO 93/05835. A sleeve-like part whose proximal edge is placed onto the skin of the user during an injection process, glides in distal direction when the injection device is displaced in proximal direction.

U.S. Pat. No. 5,609,577 describes a device that prevents a premature or unintentional penetration of the skin by the needle of an injection means.

In many cases, however, not only the visibility of the needle is a problem for patients but also the awareness that a movement of the injection device in proximal direction by the patient pushes the needle under the skin. For this reason, so-called auto-injectors were developed that automatically puncture the skin with the needle and discharge the drug after activation. Such devices are, for instance, known from EP-A-0 268 191.

SUMMARY

The invention is based on the object of providing a needle protection means for an injection device that contributes to reducing the psychological barrier of a user during an injection, in particular in case of self-injection.

The invention solves the set task with a device containing the characteristics of claim 1.

The invention is based on a protection means that surrounds the needle of an injection device. The protection means contains at least two sleeves that at least during the penetration of the needle slide at least partially over each other against a reset force active between the two sleeves.

According to the invention, the needle is only allowed to penetrate the skin once a pressure point has been overcome.

The advantages offered by the invention are mainly that the penetration of the skin by the needle of the injection device is unexpected for the user as a result of the pressure or trigger point having been overcome.

A further advantage of the invention is the relative cheap manufacture and simple operation.

BRIEF DESCRIPTION OF THE DRAWINGS

A preferred embodiment of the invention is shown in the figures:

In which:

FIG. 2a shows a side view of a means according to the invention in an operative condition.

FIG. 2b shows a frontal view of a means according to the invention in an operative condition.

FIG. 3 shows a side view of an inner sleeve.

FIG. 4 shows a path of an inner sleeve with various angles in the angled area.

FIG. 5 shows a cross section through line II—II of an inner sleeve.

FIG. 6 shows a cross section through line I—I, without injection device.

DETAILED DESCRIPTION

In the subsequent description the terms proximal and distal are used in the usual medical sense, i.e. proximal=facing towards the patient and distal=facing away from the patient.

Figure 1A:
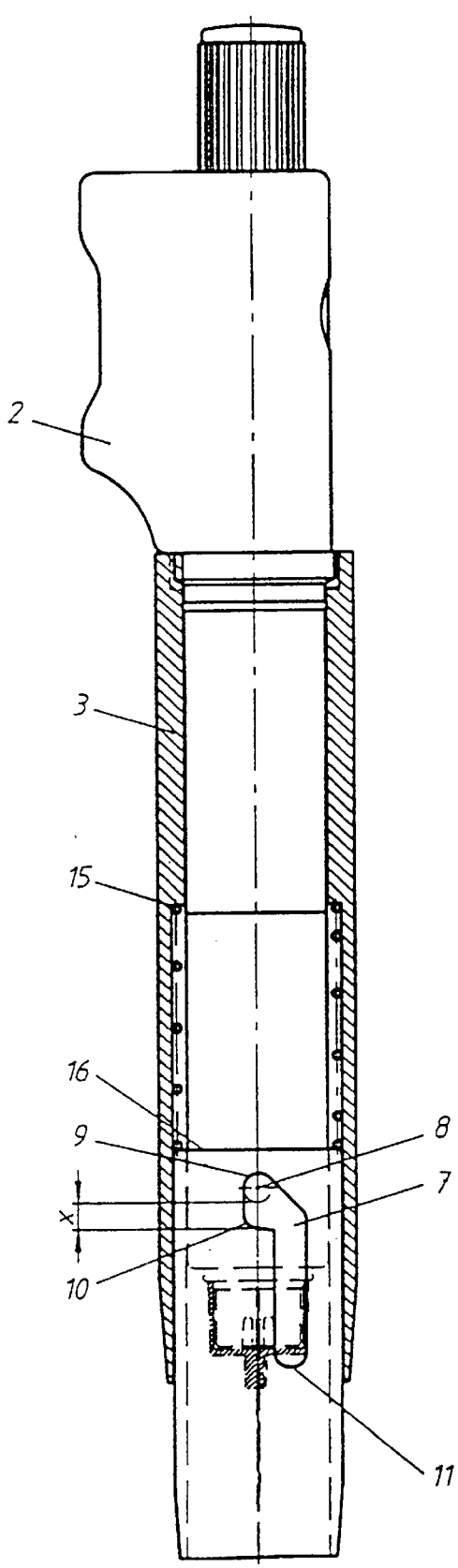
FIG. 1a shows a side view of a means according to the invention in a non-operative condition.
Figure 1B:
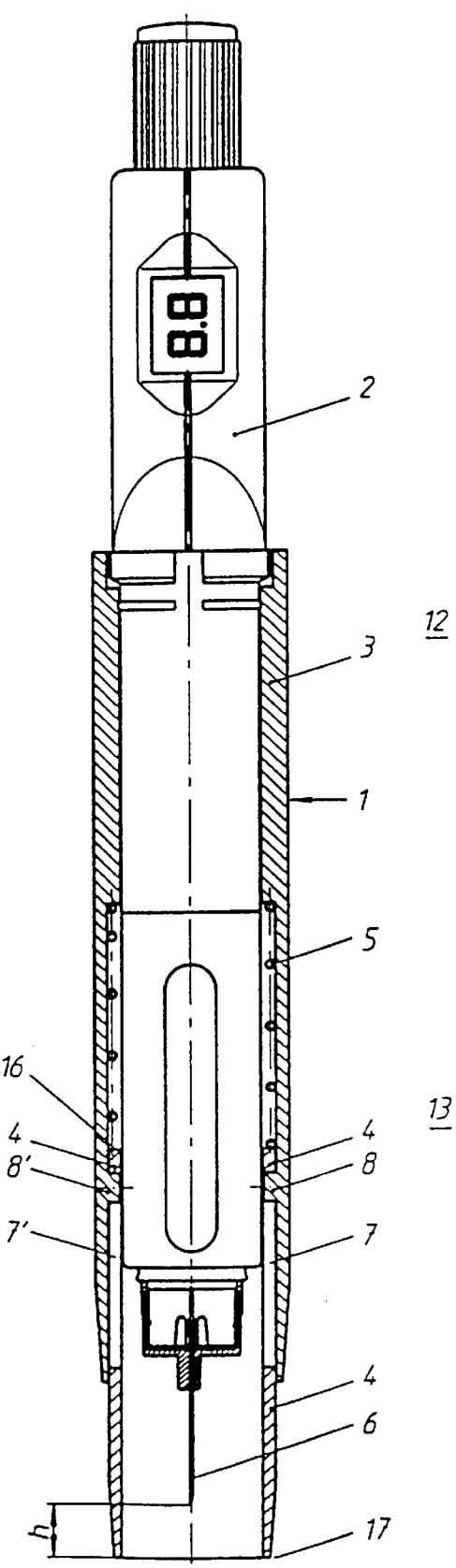
FIG. 1b shows a frontal view of a means according to the invention in a non-operative condition.

As shown in FIGS. 1a and 1b, the needle protection means 1 of the invention contains an outer first sleeve 3 located on an injection device 2 in which an inner, second sleeve 4 is arranged. The outer sleeve 3 is divided into a proximal area 13 and a distal area 12, with the distal area 12 having a smaller internal diameter than the proximal section 13.

The internal diameter of the distal area 12 of the outer sleeve 3 corresponds to the external diameter of a proximal section of the injection device 2, although it is larger by certain tolerances so that the device 1 can be slid over the proximal part of the injection device 2.

The proximal area 13 of the outer sleeve 3 contains the inner sleeve 4 and a spring 5 holding the inner sleeve 4 in proximal position by being arranged between an edge 15, formed by the decrease of the internal diameter in the transitional area between the proximal area 13 and the distal area 12 of the outer sleeve 3, and a distal edge 16 of the inner sleeve 4. The internal diameter of the proximal section 13 of the outer sleeve 3 is dimensioned in such a way that the spring 5 can be arranged between the injection device 2 and the outer sleeve 3.

The internal diameter of the proximal area 13 of the outer sleeve 3 corresponds to the external diameter of the inner sleeve 4 although it is enlarged by certain tolerances so that the inner sleeve 4 is displaceable in the proximal area 13 of the outer sleeve.

The internal diameter of the inner sleeve 4 corresponds to the external diameter of the injection device 2 (FIG. 6) and is also enlarged by certain tolerances so that the inner sleeve 4 can be displaced against the force of the spring 5 in the proximal area 13 of the outer sleeve 3 between the outer sleeve 3 and the injection device 2.

Preferably, the needle protection means 1 is coupled to the injection device 2 in such a way that the outer sleeve 3 is snapped onto the injection device 2, preventing any axial or rotational movement between the injection device 2 and the needle protection means 1. Also a bayonet joint or a threaded connection is possible as is coupling of the injection device 2 to the inner sleeve 4 of the needle protection means 1. Naturally, it is also possible that one of the sleeves 3, 4 of the needle protection means and the injection device 2 are designed as a single unit.

The inner sleeve 4 is held in the proximal position by the spring 5 arranged between the two sleeves 3, 4 so that in the non-operative condition, the inner sleeve 4 protrudes by the length h over the tip of the needle 6 of the injection device 2 in proximal direction (FIG. 1b).

The inner sleeve 4 contains at least a path 7 (FIGS. 3–5) running in the displacement direction of the inner sleeve 4, i.e. in axial direction of the device 2, that at the distal end of the inner sleeve 4 runs at an angle α towards the outside. A cam 8 of the outer sleeve 3 engages into the path 7. For stability reasons at least two paths 7, 7' should preferably be arranged diametrically opposite to each other within the inner sleeve 4 to correspondingly accommodate and guide at least two cams 8, 8' of the outer sleeve 3. This is the case in the embodiment example. In principle, however, a guide means 7 and a thus guided engaging means 8 suffice; equally, more than two of these guiding/engaging pairs can be provided that preferably cooperate again as a coulisse guide 7, 8.

Although, according to the invention, the pressure or trigger point is preferably provided by a coulisse guide and thus generated friction force, the invention does not need to be limited to this type of pressure point generation. A similar force course during puncturing could, for instance, also be generated by the design of a respective spring characteristic of spring 5.

In the non-operative position of the inner sleeve 4, the cams 8, 8' of the outer sleeve 3 are arranged in the angled area, preferably at the most distal point 9 of the paths 7, 7' of the inner sleeve 4.

If the injection device 2 and the coupled outer sleeve 3 are pushed in the proximal direction, this movement is carried out against the pressure of the spring 5. During this process, the cams 8, 8' glide from the most distal point 9 along the paths 7, 7' of the inner sleeve 4. Upon reaching the angled area 10, the cams 8, 8' force the inner sleeve 4 to make a slight rotary movement. After overcoming the angled area 10, the cams 8, 8' glide in the axially running areas of paths 7, 7' up to the most proximal point 11 of the paths 7, 7' (FIG. 2a, 2b).

The rotation movement of the inner sleeve 4 is carried out against the friction generated by the rotation of the proximal edge 17 on the skin of the user and against the friction required by the cams 8, 8' to overcome the angled area 10. The rotational movement of the inner sleeve 4 during the proximal displacement of the injection device 2 over the angled area 10 of the paths 7, 7', is made possible by the increase of the axial pressure on the injection device 2.

The friction which is generated by the rotation of the proximal edge 17 of the inner sleeve 4 onto the skin of the user can be said to be constant and is not significant for the invention. The same does, however, not apply to the force that has to be exerted so that the cams 8, 8' can overcome the friction created by the angled area 10. Depending on the angle a of the paths 7, 7' the force required for this purpose changes as the friction increases or decreases depending on the angle α. This force to be generated corresponds to the pressure or trigger point that has to be overcome to make the penetration unexpected for the user.

If the angle α of the angled area 10 is only 10°, the pressure or trigger point to be overcome is so high that a slight rotation movement on the injection device 2 or on the means 1 itself can be required to enable a proximal displacement of the injection device 2. If the angle is 30°, the pressure or trigger point to be overcome is very low. The angle must be large enough to prevent the unit from blocking, may, on the other hand, not be that large that a practically relevant pressure point can not even be created or detected.

The distance x (FIG. 1) corresponds to the path that the injection device 2 can travel in proximal direction until the cams 8, 8' reach the angled area 10 of the paths 7, 7'. The distance x is shorter than the distance h between the proximal edge 17 of the inner sleeve 4 and the tip of the needle 6. If the injection device 2 is moved in proximal direction and the cams 8, 8' reach the pressure or trigger point on the guide edge of the area 10, the distance between the proximal edge 17 of the inner sleeve 4 and the tip of the needle 6 is: h-x. This distance h-x safely prevents that the needle 6 touches or punctures the skin of the user already during the displacement of the injection device 2 in proximal direction, before the cam 8, 8' has reached the angled area 10 and thus the pressure or trigger point.

With the same overall length of the inner sleeve 4, the puncturing depth of the needle 6 under the skin can be adjusted by extending or shortening the paths 7, 7'.

If the inner sleeve 4 is in the most distal position (FIG. 2a, 2b), the user discharges the desired quantity of the drug by activating the injection device 2. When the injection device 2 is then pulled out of the skin, the inner sleeve 4 glides in proximal direction through the pressure of the spring 5. During this process, the cams 8, 8' run in the paths 7, 7' to an angled reset area 18 located opposite to the angled area 10, defining the pressure point. As soon as the cams 8, 8' run passed the reset are 18, its angle forces the inner sleeve 4 into its non-operative position (FIG. 1a, 1b) with a slight rotation. The angle of this reset area 18 remains the same, irrespective of whether the angled area 10, defining the pressure or trigger point, contains a steeper or less steep angle.

Also, different embodiments with cams (8, 8') in the inner sleeve (4) and paths (7, 7') in the outer sleeve (3) are possible.

I claim:

1. A needle protector for use on an injection device and comprising a first sleeve, a second sleeve axially slidable relative to the first sleeve and a force element between the two sleeves whereby a trigger pressure must be overcome to unexpectedly axially displace the second sleeve.

2. The needle protector according to claim 1, wherein the second sleeve can be coupled to the injection device.

3. The needle protector according to claim 1, wherein the first sleeve can be coupled to the injection device.

4. The needle protector according to claim 3, wherein the connection of the first sleeve with the injection device prevents any displacement and rotation of the first sleeve.

5. The needle protector according to claim 1, wherein said trigger pressure is created substantially by a cam and path arrangement operable generally between the first sleeve and the second sleeve.

6. The needle protector according to claim 5, wherein one of the sleeves has a plurality of cams slidably received in corresponding paths carried by the other sleeve.

7. The needle protector according to claim 6, wherein the protector has a proximal end and a distal end, and wherein a cam gliding in the proximal direction passes through at least two generally straight areas in the corresponding path, one proximal area extending in the displacement direction of the second sleeve and another area that relative to the displacement direction is distal and angled.

8. The needle protector according to claim 7, further comprising another area in the corresponding path, said another area extending generally in the displacement direction of the second sleeve, connected to the angled area and extending therefrom in a generally distal direction.

9. The needle protector according to claim 8, wherein said another area comprises a reset area.

10. The needle protector according to claim 8, wherein the angle between the proximal area and the another area creates the trigger pressure.

11. The needle protector according to claim 10, wherein changing the angle changes the force required for overcoming the trigger pressure.

12. The needle protector according to claim 11, wherein the angled area contains a guide edge for the cam slidable therein that is at an angle greater than 0 degrees and less than or equal to 30 degrees relative to the displacement direction of the second sleeve.

13. The needle protector according to claim 1, wherein one of the sleeves is provided with at least one cam which glides in a corresponding path of the other sleeve.

14. The needle protector according to claim 1, wherein the protector has a proximal end and a distal end, and wherein the trigger pressure is created by a cam and movement of the cam in an associated path, said cam urged in a distal direction as a result of the axial pressure of a spring, said cam movable through two straight areas in the associated path, one area extending in a distal direction adjacent to and at a proximal end point of the path and an angled area generally at the distal end point of the path and extending generally trasversely with respect to said one area.

15. The needle protector according to claim 1, wherein the force element is a spring.

16. The needle protector according to claim 1, further comprising a cam carried by one of said sleeves and a path carried by the other of said sleeves for receiving said cam, wherein said path comprises two generally straight areas, one of said areas extending at an angle relative to the other.

17. The needle protector according to claim 16, said straight areas comprising a first straight area extending in a distal direction adjacent to a proximal end point of the path and a second straight area generally at the distal end point of the path and extending generally transversely with respect to said first area.

18. The needle protector according to claim 17, wherein the angle between the straight areas is determinative of the trigger pressure.

19. A needle protector having a proximal end, a distal end and an axis extending generally therebetween, said needle protector comprising a first sleeve and a second sleeve, one of said sleeves axially slidable with respect to the other sleeve, and a force element operably coupling the two sleeves, whereby a pressure must be overcome to slidably displace the slidable sleeve toward the proximal end, said force element comprising at least one cam member carried by one sleeve and an associated path carried by the other sleeve for operably receiving the cam member, said path comprising a first straight region extending generally in the direction of slidable displacement and a second straight region angled with respect to the first region, and a spring operably coupled to said sleeves and urging the slidable sleeve generally toward the distal end.

20. A needle protector for use on an injection device, said needle protector having an axial length, and comprising a first sleeve and a second sleeve, one of said sleeves axially slidable with respect to the other sleeve, and a force operably coupling the two sleeves, whereby a pressure must be overcome to accomplish an injection, said force element comprising at least one cam member carried by one sleeve and an associated path carried by the other sleeve for operably receiving the cam member, said path comprising a first straight region extending generally in the direction of the slidable movement and a second straight region angled with respect to the first region, and a spring operably coupled to said sleeves and urging the needle protector to the axial length.

* * * * *